(12) United States Patent
Binnig et al.

(10) Patent No.: US 6,249,747 B1
(45) Date of Patent: Jun. 19, 2001

(54) INVESTIGATION AND/OR MANIPULATION DEVICE

(75) Inventors: Gerd K. Binnig, Wollerau (CH); Jürgen Brugger, Enschede (NL); Walter Haeberle, Waedenswil; Peter Vettiger, Langnau, both of (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/147,867

(22) PCT Filed: Jul. 17, 1997

(86) PCT No.: PCT/IB97/00895

§ 371 Date: Mar. 17, 1999

§ 102(e) Date: Mar. 17, 1999

(87) PCT Pub. No.: WO94/29894

PCT Pub. Date: Dec. 22, 1994

(51) Int. Cl.[7] ............................. G01B 7/34; G01N 25/72; G11B 11/00

(52) U.S. Cl. ..................... 702/33; 73/105; 369/126

(58) Field of Search ................... 702/33, 36; 250/306, 250/307; 369/126, 44.28–44.34; 73/105, 651

(56) References Cited

U.S. PATENT DOCUMENTS

| | | | | |
|---|---|---|---|---|
| 5,808,302 | * | 9/1998 | Binnig et al. | 250/306 |
| 5,856,967 | * | 1/1999 | Mamin et al. | 369/126 |
| 5,877,497 | * | 3/1999 | Binnig et al. | 250/306 |
| 6,079,255 | * | 6/2000 | Binnig et al. | 73/105 |
| 6,092,422 | * | 7/2000 | Binnig et al. | 73/651 |

* cited by examiner

*Primary Examiner*—Kamini Shah
(74) *Attorney, Agent, or Firm*—Ronald L. Drumheller

(57) ABSTRACT

An investigation and/or manipulation tool for a sample which is locally deformed when subjected to a local heat treatment includes a power supply for heating a tip of the tool wherein the tool has a structure such that the power supplied to the tip heats substantially only the tip of the tool and includes a region of relatively high heat conductivity that provides fast cooling of the tip when power is not supplied to the tip.

25 Claims, 4 Drawing Sheets

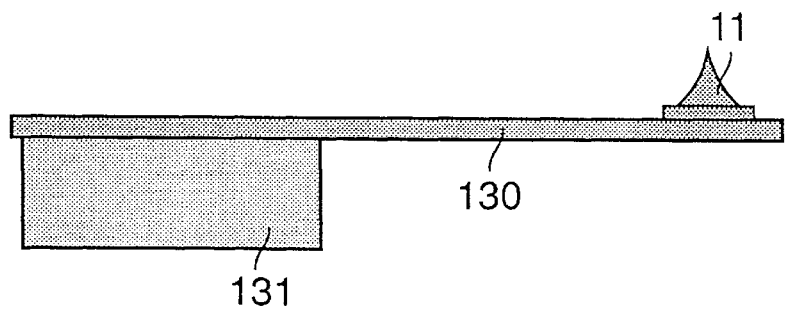
Fig. 4a
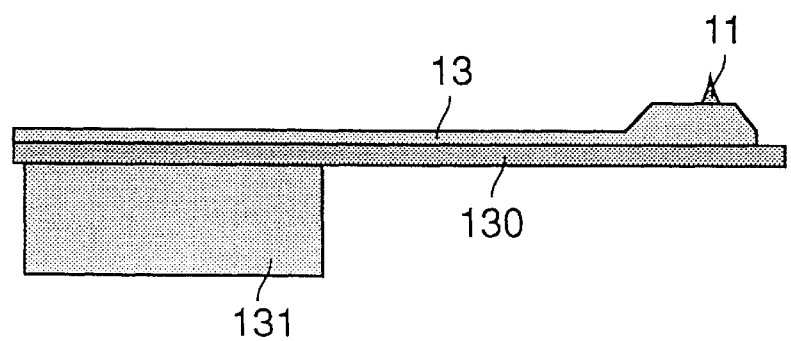
Fig. 4b
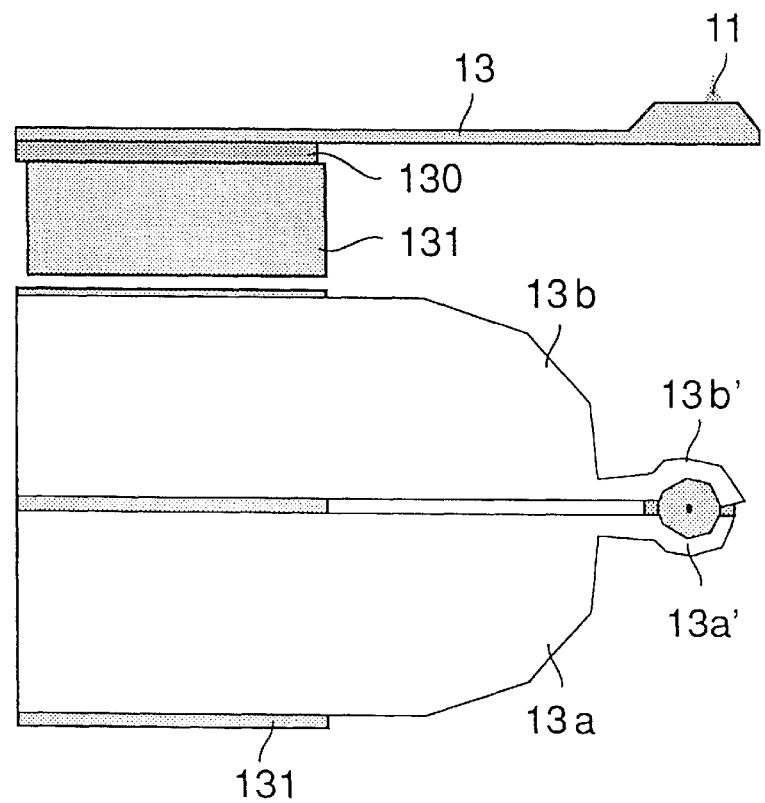
Fig. 4c
Fig. 4d

INVESTIGATION AND/OR MANIPULATION DEVICE

TECHNICAL FIELD

The invention relates to an investigation and/or manipulation device for a sample, wherein the sample consists of a material that is locally deformed when subjected to a local heat treatment. More particularly, the invention relates to a data storage system with a fast reading and writing scheme based on atomic-force microscope (AFM) techniques. A further essential aspect of the invention has to be seen in the provision of an improved sensor which is able to detect the displacement of a movable object relative to an immovable object.

BACKGROUND OF THE INVENTION

A conventional investigation device for a sample is e.g. disclosed in U.S. Pat. No. 5,345,815. In particular, this known investigation device relates to an atomic-force microscope (AFM) which comprises a cantilever, the movement of which is picked up by means of a piezoresistive deflection sensor.

An AFM is known as an instrument in which a flexible cantilever of very small dimensions is moved relatively to a surface so as to investigate or to scan the structure of this surface. Such cantilevers typically have a sharp tip at the free (distal) end thereof. The apex of the tip projects in the direction of the sample surface. As the sample is scanned, forces (including electrostatic, magnetic, viscous, van-der-Waals and other forces) between the cantilever tip and the sample surface cause the cantilever to deflect. The deflection is measured by the integrated sensor (as e.g. the piezoresistive deflection sensor disclosed in U.S. Pat. No. 5,345,815); the output signal of this sensor is representative of the respective profile or structure of the sample and, typically, has an extraordinary resolution in the order of nanometers.

A similar type of AFM which makes use of integrated piezoresistive sensors is disclosed in the PCT Patent Application No. WO 94/298994; furtheron, an AFM device which measures the deflection of the micro-cantilever by means of an optical sensor instead of piezoresistive elements is disclosed in U.S. Pat. No. 5,388,323.

However, these known AFM devices are only capable of investigating or scanning the surface of a sample; these known AFM devices are, however, not capable of manipulating the surface. The presently known AFM devices, consequently, cannot be used for writing information onto the surface of a storage medium. On the other hand, it would be highly desirable to provide a device which both has the ability to investigate and to manipulate a sample, for example in order to provide a read/write operation for coded information on the sample.

Since an AFM is able to investigate a sample with a resolution in the order of nanometers, such an AFM device is able to read the information stored on a very small area; hence, an AFM device, in principle, has the ability to read huge amounts of information which are stored at a very high recording density. However, the investigation techniques used in these known AFM devices are not fast enough so as to be used for a read operation having a sufficiently high data transfer speed (throughput). Moreover, the power consumption of the sensor of these known devices is rather high; therefore, any attempt to speed up the data transfer rate by using a plurality of AFM tips simultaneously is drastically limited by the increasing power consumption which finally would lead to an overheating of the device.

OBJECT OF THE INVENTION

Accordingly, it is the object of the present invention to provide an investigation and/or manipulation device which is able to investigate and/or to manipulate a sample at a very high speed and with a very low power consumption.

Another aspect of the present invention is to provide a data storage system that advantageously uses this investigation and/or manipulation device in order to significantly increase the recording density as compared to conventional data storage systems.

Still another aspect of the present invention is the provision of a new and improved sensor for detecting the displacement of a movable object relative to an immovable object which has a very high detection speed and a low power consumption.

SUMMARY OF THE INVENTION

The core concept underlying the investigation and/or manipulation device of the present invention as claimed in claim 1 is the provision of a heated tool which is made in such a way that the supplied power is heating substantially only the tool, and not the complete structure of tool and the support means (cantilever). This exclusive heating of the tool can easily be reached if the tool and the cantilever are formed with an appropriate structure or if these parts are made of appropriate materials; thus, as claimed in claim 3, this exclusive heating of the tool can e.g. be reached if at least that one region of the cantilever which is in the neighbourhood of the tool is made of a material which has a lower heat conductivity than the material of the tool; alternatively, as claimed in claim 9, it is possible to provide a cantilever which is made of two arms, these two arms being spaced from each other and being made of electrically conductive material, each arm, at the outer end thereof, being connected to the tool so as to supply electric power in order to heat same. The latter-mentioned solution has the additional advantage that any bimorphous effects that could deform the cantilever can be avoided; furthermore, the overall mass of the moved parts of the device is further reduced, thereby further increasing the operating speed.

As, according to the afore-mentioned basic principle of the present invention, the investigation and manipulation process is performed by a heated tool which is isolated with respect to the support means (preferably in the form of a cantilever) and, thus, the only part of the device to be heated, the power consumption of the device, due to the small mass of the tool as compared to the mass of the cantilever, is extremly low. Consequently, the heating and cooling of the tool can be performed at very short cycles so that the work speed of the device is very high; the investigation and/or manipulation of a sample, thus, can be perfomed at an extraordinary high speed. Experiments have e.g. shown that operation frequencies of up to 1 MHz or even more can be realized without any problems.

Of course, if the device of the present invention is operating in the manipulation mode, the respectivly manipulated sample—due to the afore-mentioned operation principle of the tool—should consist of a material which is locally deformed when subjected to a local heat treatment. For this operation mode, the device of the present invention, moreover, comprises a manipulation means which is adapted to supply a high amount of power to the tool, this high amount of power heating the tool to a temperature which is sufficient to deform the sample surface region which is presently effected by the tool.

One further major advantage of the present invention has to be seen in the fact that the heated tool not only can be used for manipulation purposes but also for sensing the structure of the sample: Experiments made by the inventors have revealed that it is possible to detect or investigate the structure of the respective sample by heating the tool to a predetermined temperature (which, of course, must be unsufficient to deform the sample) and by subsequently measuring a variation in the temperature of the tool; it in fact could be shown that the cooling rate of the tool is influenced by the structure of the sample to such an extent that the corresponding change of the temperature of the tool can be easily measured (e.g. by measuring the corresponding change or variation of the power supplied to the tool, see claim 12). Therefore, the heated tool can also be used as a sensor for investigating the structure of the sample.

Thus, if the device of the present invention is operating in the investigation mode, there is provided a sensing means which is adapted to supply a low amount of power to the tool, this low amount of power being selected such that it is insufficient to locally deform the sample, the sensing means further being adapted to detect a variation in temperature of the tool as being indicative of the surface structure of the sample. In this context, one further advantage of the present invention has to be seen in the fact that the sensor signal obtained by such a sensing means has a comparatively good signal-to-noise ratio which, in any case, is better than that of the output signal of a piezoelectric sensor as used in the afore-mentioned prior-art devices. Due to this excellent signal-to-noise ratio it is easily possible to operate a multitude of heated sensor tools on a very small space so that parallel operation of the device for further speed enhancement is no problem at all. Consequently, the afore-mentioned basic concepts of the present invention allow to realize very high data transfer rates.

Since the present invention is able to perform both operation modes (investigation and manipulation process) by using one and the same means, i.e. a tool which is heated while being isolated with respect to the supporting cantilever, it moreover is possible to realize the device of the present invention by a system which is mechanically and electronically very simple. Hence, the manufacturing of the device of the present invention can be advantageously facilitated and therefore will be more reliable. For manufacturing the device of the present invention, well known methods (as e.g. lithographic processes) can be used; thus, the device of the present invention can be manufactured with high reliability and effectiveness.

In order to further improve the working speed of the device of the present invention it is possible to provide a layer having a high heat conductivity in the vicinity of the tool; this additional region has the function of a cooling region which increases the cooling rate of the tool, thereby advantageously further increasing the operating frequency of the device. Such a cooling region could e.g. be realized by a layer of silicon which is provided at that side of the cantilever which is opposing the tool.

One further advantage of the investigation and/or manipulation device of the present invention has to be seen in that the tool can be a tip which is similar to the tip which is used in the conventional atomic-force microscopes as described hereinbefore. Thus, major parts of the peripheral means and equipment of the device of the present invention, such as the positioning means for positioning the cantilever and thereby the tool relatively to the sample, can correspond to those well-known means. Therefore, the manufacturing costs of the device of the present invention can be further decreased.

The afore-mentioned device of the present invention, although being a general-purpose means for investigating and/or manipulating samples of different kinds, is especially useful for providing a novel storage system which is able to read and write information at very high speed and extremly high storage density. In this case, the sample preferably is a storage medium in the form of a very thin soft layer (such as a layer made of PMMA in a thickness of e.g. 30 nm), the afore-mentioned "manipulation" being the formation of storage pits of a predetermined size (preferrably in a size roughly corresponding to the size or diameter of the apex of the tip) and the "investigation" being a sensing operation as to whether each predefined storage location comprises such a pit (i.e. an information bit "1") or not (information bit "0").

This novel storage system according to the present invention, due to the very low power consumption and, in addition, due to the high resolution obtained by the heat sensor means, can be optimally used for a parallel reading/writing scheme. Thus, the storage system of the present invention not only allows to obtain an extremly high storage density but also enables a very high data throughput which is directly proportional to the number of reading/writing tips that are used in parallel. Assuming that a number of 1000 or even more parallely used tips seems to be realistic, and further assuming a basic clock frequency of about 1 MHz (see the explanations above), one can come to the conclusion that a data throughput of as much as 1 TBit per second (or even more) could easily be realized by the storage system of the present invention.

Such a parallely operated storage system, advantageously, is based on the use of a plurality of support means (such as cantilevers) which are arranged in form of a matrix, each support means having a read/write tip mounted thereon. This matrix basically corresponds to the single magnetic head of a conventional magnetic-storage hard disk. Thus, the storage system of the present invention could be based on a structure which, basically, consists of a a swivel arm for moving the matrix of tips relative to the thin soft storage layer, the storage layer itself being formed on a disk which is turned by means of an electric motor. Therefore, this storage system could be realized on the basis of structures which are well known from the field of magnetic-storage hard disks so that the development of corresponding mechanical parts should be comparatively easy.

According to yet another aspect of the invention, the afore-mentioned principle of heating a movable object (such as the tool or tip of an investigation device) to a predetermined temperature and to detect the cooling rate of this movable object which is caused by the structure of an immovable object in the vicinity thereof can be used to provide a novel sensor which has a very high sensitivity with respect to any displacement occuring during a surface scan. Due to the described characterisitics of such a sensor, the sensor suggested by the present invention in addition has a very high operating speed so that any instrument equipped therwith is able to provide the desired observation results in a very short time. This sensor advantageously can be realized by forming the heated movable object at a first end portion of a cantilever, the cantilever at the second end thereof being movably fixed with respect to the immovable object; in other words, this sensor would basically correspond to an AFM in which the tip is heated so as to serve as a sensor for detecting the displacement of the cantilever.

If the afore-mentioned sensor is part of a storage system in which, as described hereinabove, the surface structure has a rather regularly structured profile consisting of nearly identical pits, there is no danger that the measurement result could be negatively influenced by major objects in the vicinity of the present detection location. If, however, the afore-mentioned sensor is part of an AFM, the object under observation therefore having a quite irregularly structured surface (as is the case in most samples), it cannot be excluded that the sensor is additionally cooled by a comparatively huge object, even if that object is in a certain distance of the present detection location. In such a case this additional cooling would unavoidably falsify the sensor signal so that the sample cannot be correctly scanned.

In order to avoid the above mentioned problem, the present invention suggests to provide a sensor the cantilever of which is coupled to the movably fixed end of the cantilever of an AFM in such a way that the displacement of the AFM cantilever is transferred to a corresponding displacement of the sensor cantilever. Consequently, the cooling rate of the sensor cannot be influenced by major objects of the sample surface. This solution, moreover, has the advantage that the heat generated by the sample cannot influence the sample surface so that the sensor also can be used for scanning very heat-sensitive samples.

With respect to further advantageous further developments of the invention, reference is made to the subject-matter of the subclaims.

BRIEF DESCRIPTION OF THE DRAWINGS

In the following, some embodiments of the present invention are described in detail with reference to the accompanying drawings by way of example. In the drawings:

FIGS. 4a through 4d show a second embodiment of the investigation and/or manipulation device and a method for producing same;

DETAILED DESCRIPTION OF THE INVENTION

In the following, an embodiment of an investigation and/or manipulation device constructed in compliance with the principles of the invention is described with reference to FIGS. 1 through 3; in these figures, similar or identical parts or elements are of course depicted with the same reference numbers. In the described embodiment, the investigation and/or manipulation device is used to read and write information from respectively onto a storage medium in form of a thin layer (the storage system shown in FIGS. 4 and 5, in fact, using a plurality of such devices). Therefore, the subsequently described embodiment of the investigation and/or manipulation device of the invention, for the sake of simplicity, in the following will be referred to as "storage device"; it is, however, to be noted that the principles of this device are applicable for other apparatus as well; the described embodiment, therefore, also could be part of an atomic-force microscope (AFM) or of a tool for manufacturing nanostructures ("nanolithography").

Figure 3:
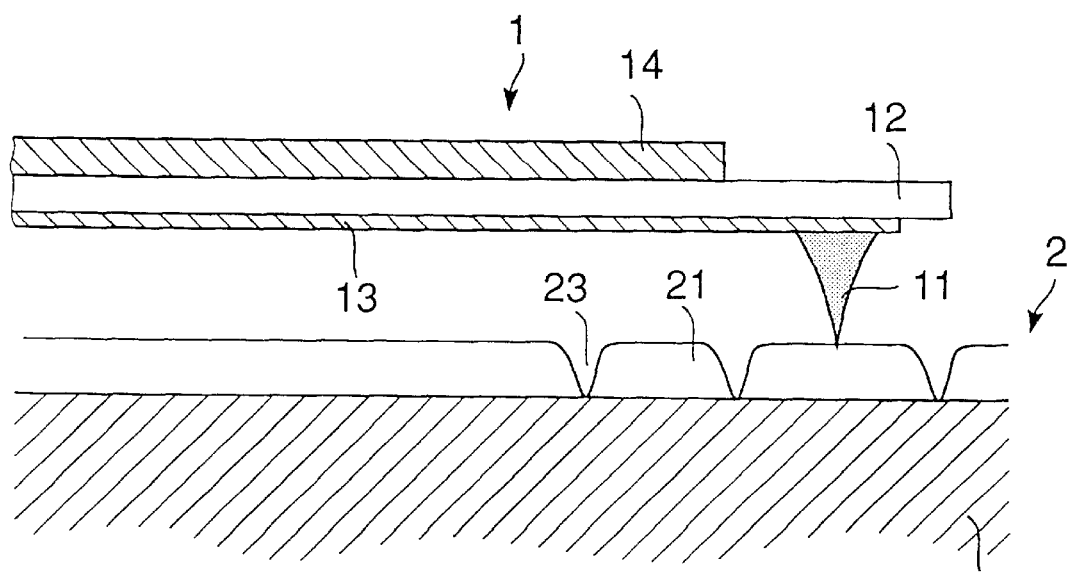
FIG. 3 shows the device of FIGS. 1 and 2 during the scanning of a sample which is to be investigated and/or manipulated.

In FIG. 3, the relative position of the storage device (generally depicted with reference numeral 1) with respect to a storage medium 2 ("sample") is shown. The storage device comprises a cantilever 12 which is similar to the cantilever as used in an AFM; at the free or distal end of the cantilever 12 a read/write tip 11 orthogonally projecting from the cantilever 12 towards the storage medium 2 is provided (the tip 11, thus, corresponding to the "investigation and/or manipulation tool" in the terms of the appended claims). The cantilever 12, therefore, has the function of a support for the tip 11; however, other types of support means, such as spring elements or a diaphragm, may be used as well; in any case, the respective support means must be able to move the tip 11 relatively (i.e. substantially in vertical direction) to the surface of the sample 2.

The cantilever 11 is movably borne in a positioning means (not shown) which positions the cantilever 11 relative to the storage medium 2. The basic construction of such a positioning means is known to those skilled in the art and, therefore, will not be described in more detail.

Figure 1:
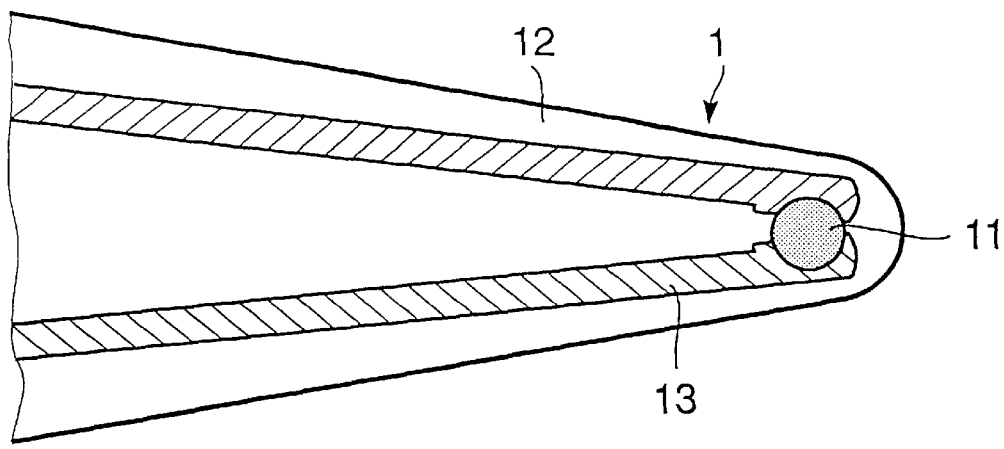
FIG. 1 shows a plan view of an embodiment of the investigation and/or manipulation device according to the present invention.
Figure 2:
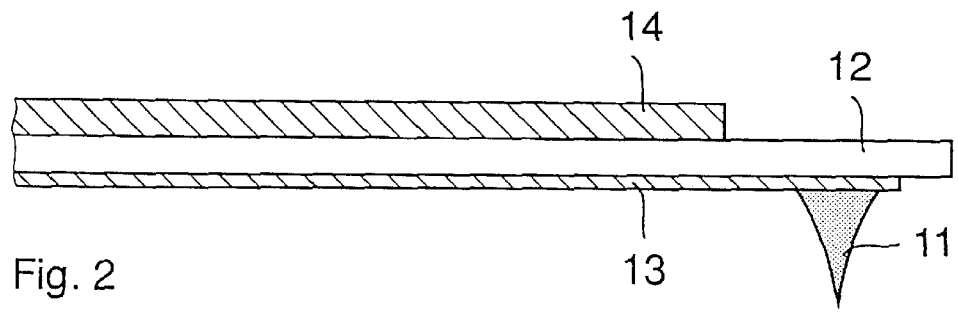
FIG. 2 shows a side view of device shown in FIG. 1.

As can be gathered from FIGS. 1 and 2, the read/write tip is formed on a substrate layer of electrically and thermally poorly conducting material which is the basic substrate of the cantilever 12; this poorly conducting material preferably is made of silicon dioxide ($SiO_2$). The tip 11 projects with its apex or distal end in the direction of the storage medium 2; although the projection angle of the tip 11 relative to the surface of the storage medium 2, in these figures, is shown as 90°, this angle may be in the range from e.g. 60° to 120°, depending on the weight, the support and the flexibility of the cantilever 12. The tip 11 is preferably made of doped or not doped silicon (Si).

In this embodiment of the invention, the power supply means comprises a pair of contact lines 13 (e.g. metal lines) that are formed on a surface of the $SiO_2$ layer of the cantilever 12; as these contact lines 13, at the outer end thereof, are contacted to the tip 11, they are able to supply current to the tip 11. Thus, the tip 11 is heated by the current flowing through the contact lines 13 and the tip 11. In the vicinity of the tip, a layer 14 having a better heat conductivity than the layer 12 is formed. This additional layer provides a better cooling ratio of the region where the tip 11 is located and, therefore, leads to a better cooling of the tip 11 which, in turn, allows to improve the operating speed (i.e. the data throughput of the storage device). The additional layer 14 which preferably consists of Si is located on that side of the cantilever 12 which is opposed to the contact lines 13 so as to avoid any shortcircuiting thereof.

As illustrated in FIG. 3, the storage medium 2, on the surface thereof, comprises a thin soft layer 21 which is directed to the apex of the tip 11 and which is used to read and write information in the form of single pits, each individual pit representing a binary information (bit). The soft layer 21 consists of a material which is easily deformed by the tip 11 when subjected to heat treatment. In the described embodiment, the soft layer 21 is made of polymethyl-methacrylate (PMMA) and the thickness of the layer is preferably about 30 nm. The layer, however, also could be made of another thin film, such as a metal film, which is not as soft but comparatively hard; in any case, the material of the thin film hast to be deformable by a heat treatment.

Underneath the thin layer 21, there is provided a substrate 22 which is not responsive to the afore-mentioned heat treatment of the soft layer 21 during a write operation. In this embodiment, the material of the layer 22 is Si, thereby providing a fast cooling of the thin layer 21. In FIG. 3, by way of example, there are shown two deformed portions 23 of the soft layer 21, each portion 23 representing a single storage pit.

The described storage device 1 further comprises a (not shown) manipulation means for a controlled manipulation of the storage medium 2 by a heat treatment (write mode), and sensing means for scanning the surface of the storage medium 2 by detecting variations in the temperature of the tip 11 so as to detect the presence or absence of storage pits (read mode). The electronic power supply and hence the tip 11 are operable in two different modes (reading and writing) which differ from each other in the amount of the supplied power. Depending on the relative amount of power, the tip 11 is either writing pits into the thin layer (high amount of power, write mode) or detecting the presence or absence of written pits (low amount of power, read mode).

In the following, the operation of the foregoing embodiment of the present invention during the two operation modes will be described in more detail.

In the read mode, the tip 11 is supplied with a predetermined amount of current through the (not shown) power supply means and the contact lines 13. The current that passes through the tip 11 heats the tip 11 to a predetermined temperature, which process is controlled by the afore-mentioned control means. By monitoring the current that is heating the tip 11, a certain resistance value can be derived. As the supplied power has a predetermined value, the resistance of the tip 11 shows a predetermined value that is measured with a measuring circuit (not shown). Preferably, the predetermined amount of power is selected such that the corresponding resistance value can be readily and reliably measured. As a result of the heating of the tip 11, there is provided a temperature gradient in the close vicinity of the tip 11. This resistance value is, however, depending on any variation of the temperature of the tip 11. Therefore, whenever the temperature gradient of the tip 11 is varying depending on the distance between the tip 11 and the surface of the storage medium (i.e. the thin film 21), the resistance value of the heated tip 11 varies accordingly.

It is to be noted that, instead of the supply of a predetermined current, a suitable voltage supply may also be taken into account; however, due to the varying resistance value of the tip 11 with temperature, a constant-current supply, in many cases, may be the better approach.

In a similar manner as a conventional AFM that is operated in contact mode, the cantilever 12 together with the heated tip 11, under the control of the positioning means, is scanning over the surface of the storage medium 2 that carries the coded information in the thin layer 21 thereof. As long as the tip 11 is moving along a substantially plain surface (i.e. a region of the thin layer which has no information pit 23 formed therein), the tip 11 is not subjected to any signifcant variation in its temperature gradient and hence no signifcant variation in its resistance value is measured; conseqently, the output signal is interpreted as being representative of the information bit "0". If the tip 11, however, reaches a portion of the soft layer 21 where a deformed portion 23 or pit previously has been recorded, the tip 11 is subjected to a signifcant variation in its temperature gradient and hence a signifcant variation in the resistance value is measured; conseqently, the output signal is interpreted as being representative of the information bit "1". In this way it is possible to easily read the coded information written in the thin film 21 in the form of pits 23. Subsequently, further circuitries transform the output signal of the tip 11 into an information signal which can be further processed in a computer or the like.

Generally, if the tip 11 comes closer to the sample 2, i.e. if the tip is cooled more efficiently through the gas (air) in the medium between the tip and the sample, additionally the contact area increases whenever the tip 11 enters a pit, resulting in the same effect of an increased cooling effect.

In the write mode, the tip 11, through the power supply means and the contact lines 13, is also supplied with a current. However, in contrast to the read mode, the current supplied during the write mode is a pulse train corresponding to the binary information to be written onto the thin film. If the binary information has the logical value "0" (false), no current is supplied to the tip 11 and, accordingly, no pit is formed at the present recording location of the tip 11. If the binary information to be written onto the thin film, in contrast thereto, has the logical value "1" (true) a current pulse having a predetermined duration and power level is supplied to the tip 11; the duration and current strength of this pulse is selected such that a pit 23 is formed which has a predetermined depth and width; the width basically corresponds to the diameter of the tip 11 whereas the depth is preferably selected such that the apex of the tip 11 does not touch the comparatively hard surface of the substrate 22 of the storage medium 2. By this measure, i.e. by avoiding any contact with the surface of the substrate 22, undue wear of the tip 11 can be avoided so that the storage device has a very long life duration.

Alternatively, it is possible as well to apply a predetermined small amount of power (i.e. a kind of bias power) during the recording of the logical value "0" (false), this amount of power, of course, being selected such that the surface of the thin layer 21 is not deformed. However, due to this bias voltage, the difference in the supplied power between the logical values "0" and "1" is smaller than in the afore-described embodiment so that the tip 11 is subjected to less thermal stress.

In summary, in both operation modes (reading and writing) the tip 11 of the cantilever 12 is heated by a power supply means which is supplying a current to the tip 11, the current being individually controlled depending on the present operation mode. In the write mode, the amount of current required to form a pit on the surface of the soft layer 21 is higher than in the read mode.

Thus, the described storage device is able to write and read information that is stored in the soft layer of the storage medium, the coded information having a size in the order of nanometers only. Hence, a very high recording density can be achieved.

Since the mass of the tip 11 is very low, the heat amount which is necessary to deform the soft layer 21 in the write mode is reached in a very short time which results in a high write speed without overheating of the tip 11. The low mass of the tip 11 also leads to a low power consumption of the storage device even in the write mode. Typically, a power consumption of as low as $10^4$ Watt can be expected.

As already mentioned above, the additional layer 14 provides a better cooling ratio of the region at which the tip 11 is located and, therefore, leads to a better cooling of the tip 11 which, in turn, allows to further improve the operating speed of the storage device. In practice, operating frequencies of more than 1 MHz seem to be realistic.

The previously described embodiment of the storage device—depending on the respectively used materials—might have the disadvantage that the different thermal stress of these materials could lead to a bimorph effect, i.e. to a bending of the cantilever. Therefore, in an alternative embodiment of the storage device of the present invention, the cantilever 13 is made of two individual arms the form and extension of which basically may correspond to the form of the contact lines shown in FIG. 1. These two separate arms are spaced from each other and are made of electrically conductive material, each arm, at the outer end thereof, being connected to the read/write tip 11 so as to supply electric power to the tip 11. The two arms 13, thus, are integrated part of the power supply means.

The thickness of the two arms 13, of course, will have to be selected such that this "cantilever" is able to withstand all forces which act during the read and write cycles. Due to the very low mass of such a two-arm cantilever system it is, however, to await that it will be possible to provide comparatively thin cantilever arms; therefore, the total mass of the read/write system is further reduced, thereby further increasing operating speed.

A preferred embodiment of such a two-arm-cantilever and a method for producing same is shown in FIGS. 4a through 4d, the FIG. 4d thereof showing the final cantilever/tip structure.

According to FIG. 4a, in a first production step, there are provided a socket 131 and a cantilever 130 which both are made of $SiO_2$. At the outer end of the cantilever 130, a tip 11 is formed which consists of Si. If necessary, the cantilever may be formed without the socket 131.

In a second step (see FIG. 4b) two flat arms 13a and 13b of electrically conducting material such as copper are formed on the top surface of the cantilever 130. The form of these arms 13a and 13b can be derived from the top view of FIG. 4d: Hence, these arms are relatively broad at their major extension whereas the arm regions 13a' and 13b' which are contacting the tip 11 are comparatively narrow. Due to this geometry of the two arms 13a and 13b, the heat generated in the tip 11, on the one hand, basically is concentrated on the tip 11 (i.e. other regions are heated to a negligible extent only) and the broad parts of the arms, on the other hand, are an effective cooling device so that the heat generated by the tip 11 is removed as fast as possible; consequently, the device of FIG. 4 can be operated at very high frequencies.

In a final step, as shown in FIG. 4c, the supporting cantilever 130 is removed from those parts of the arms 13a and 13b which are not above the socket 131. Therefore, the two arms 13a and 13b have a very low mass, thereby forming a "cantilever" 13 which is rather light. Moreover, at those regions where the heat is generated, no thermal stress which acts in the perpendicular direction will be applied to the cantilever arms 13a and 13b so that the device can be operated in a reliable mode.

The afore-mentioned steps for producing the cantilever/tip structure can be performed by well known methods, such as lithography and etching used in the production of semiconductor devices.

As already mentioned above, the described embodiment of the investigation and/or manipulation device of the invention also could be part of an atomic force microscope (AFM) or of a tool for manufacturing nanostructures ("nanolithography"). In the latter case, of course, the power supplied in the manufacturing mode of operation might have an analogue form corresponding to the respective depth of the nanostructures to be formed.

When operated as a storage device, as has been described hereinbefore with reference to FIGS. 1 through 4, the device of the present invention, due to its very low power consumption and, in addition, due to the high resolution obtained by the novel heat sensor tip, can be optimally used for a parallel reading/writing scheme. An embodiment of such a parallelly reading and writing storage system will be described in the following with reference to FIGS. 5 and 6.

Figure 5:
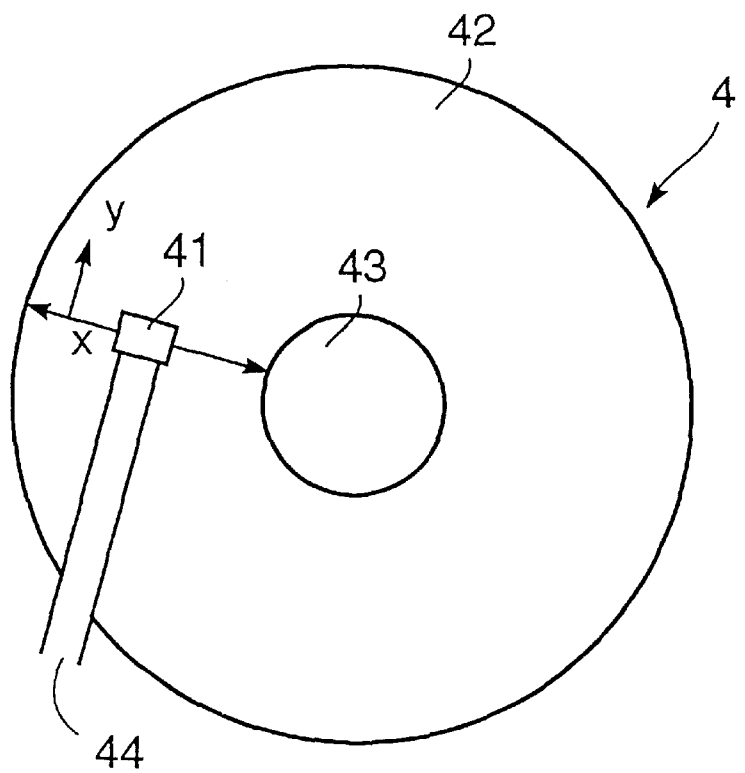
FIG. 5 in a plan view schematically shows the basic structure of a data storage system which is based on the usage of a plurality of investigation and manipulation devices in accordance with the invention which are arranged in the form of a matrix.
Figure 6:
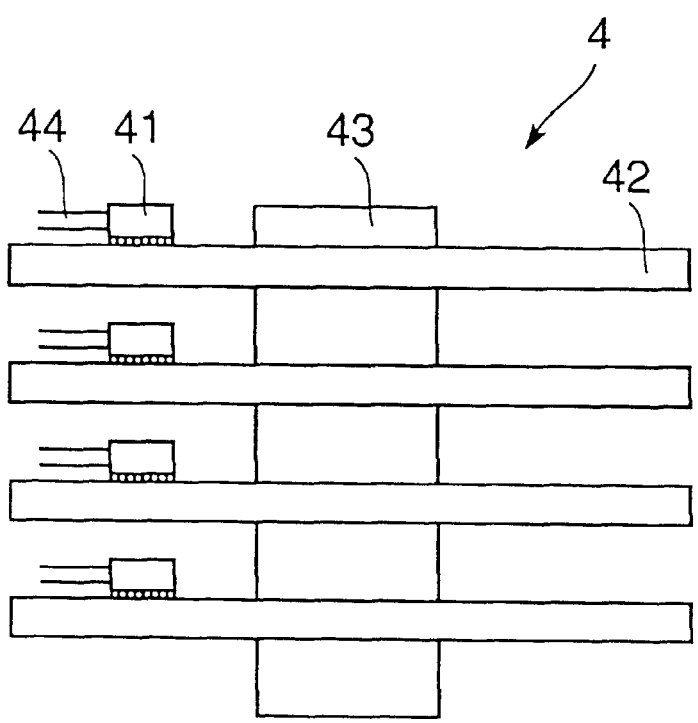
FIG. 6 shows the data storage system of FIG. 5 in a side view.

According to FIGS. 5 and 6, the described embodiment of a storage device 4 comprises a stack of four storage disks 42 which are rotatably mounted by means of a shaft 43 which is driven by a (not shown) electric motor. The upper surface of each storage disk 42 comprises a thin film layer corresponding to the layer 21 of the storage medium shown in FIG. 3; this thin film layer is the recording surface and, functionally, corresponds to the magnetic surface of a hard disc.

The thin film layer of each storage disk 42 is scanned by a swivel arm 44 which is rotatably mounted at the outer end thereof; thus, by means of a (not shown) electric motor, the swivel arm 44 can be moved in radial direction over the surface of the corresponding storage disk 42 along a somewhat curved path which is denoted with "x" in FIG. 4. As the displacement in the orthogonal direction "y" is achieved by an appropriate rotation of the storage disk 42, the inner end of the swivel arm 44 can be exactly positioned at any location of the surface of the storage disk 42.

At the inner end of the swivel arm 44 a plurality of storage devices, each of which has a construction similar to that described in FIGS. 1 through 4 (i.e. having a cantilever/tip structure), are mounted in a matrix-like arrangement 41. The matrix 41 may incoporate as many as 1000 or even more individual storage devices. For the purposes of the following description it shall be assumed that the matrix 41 is an arrangement of e.g. 32×32 (i.e. 1024) individual storage devices each of which is made of a cantilever and a tip at the outer end thereof, the cantilever being mounted at a wall of the corresponding cell of the matrix structure. The outer dimensions of the matrix 41 may e.g. be 1 mm×1 mm so that each individual storage tip would have a storage area of about $10^{-3}$ mm$^2$. Further assuming that each tip is able to read/write a total of 1000×1000 pits within this small area, one comes to the conclusion that the storage system of FIGS. 5 and 6 has a storage density of at least about 1 TBit per mm$^2$. The read/write signals of each storage tip could e.g. be transferred to an external control electronic unit by means of a common multiplex system as it is used in CCD-devices.

The afore-mentioned described storage system of the present invention may be operated as follows: First, the matrix 41 is moved by means of the swivel arm 44 to a certain position in the radial (x) direction (i.e. a positioning movement that corresponds to the track search in a conventional hard disk). The sector of interest within this track is positioned by suitable movment of the disk 42. In this way the matrix 42 is positioned at a specific square sector, i.e. at a region that corresponds to the 1 mm$_2$ size of the matrix.

Having been positioned within this storage sector, the matrix 41, by a combined movement of the swivel arm 44 and a movement of the disk 42, in a stepwidth of about 32 nm can be finely displaced in such a way that all pit positions within each cell of the matrix 41 are precisely positioned. In detail, when having been positioned within the storage sector, both the swivel arm 44 and the disk 42 are mechanically locked at these positions by means of suitable clamping means. The clamping means of the swivel arm 44, furthermore, comprises an elastic support such as a spring element; thereby, by applying a predefined power to the drive of the swivel arm 44, the swivel arm 44 will perform a rapid swinging movement in the x direction within the locked sector by which swinging movement all pit positions in x direction within each cell of the matrix 41 are scanned. On the other hand, the clamping means of the disk 42 comprises a damping element and the motor of the disk is also supplied with a predetermined power in such a way that the matrix is moved in the y direction within the locked sector at the same time at which the swivel arm is performing 1000 swing movements. Thus, all 106 pits within each cell are scanned.

In the read mode, all tips are heated to the predetermined read temperature and, at each pit position, the stored information is read simultaneously by all tips. In other words, 1024 bits are read in one read cycle. In the write mode, the same movement is performed and 1024 bits are written within one cycle. Due to this parallel read/write scheme an extraordinarily high data transfer rate can be realized.

Of course, the afore-mentioned read/write process is performed by all stacked swivel arms simultaneously so that the data transfer rate is further increased.

The afore-mentioned advantages of the storage system mainly are based on the advantageous features of the heated tip according to the present invention. Thus, due to the low power consumption and the short cool-down period of this novel tip, a fast read/write operation speed can be obtained which in turn leads to a high data throughput.

In the following, a further embodiment of the present invention will be described; this embodiment relates to an improved displacement sensor for an AFM.

As already pointed out hereinabove, the basic concept of the present invention in the form of a heated tip can also be used for an investigation device, e.g. in the form of an atomic force microscope (AFM). In this case, the tip and the supporting cantilever of such an AFM could be replaced by the novel tip/cantilever construction as shown in FIGS. 1 and 2.

In this case, however, i.e. if the heated sensor tip is part of an AFM, the object under observation has a quite irregularly structured surface (as is the case in most samples); it therefore cannot be excluded that the sensor is additionally cooled by a comparatively huge object, even if that object is in a certain distance of the present detection location. The temperature distribution around the tip e.g. is more or less effected by close elevations or hollows in the surrounding area. In such a case this additional cooling would unavoidably falsify the sensor signal so that the sample cannot be correctly scanned.

This problem can be solved by the two embodiments of an AFM in accordance with the invention which in the following are described with reference to FIGS. 7 and 8, respectively. These two embodiments have in common the feature that the displacement of the AFM tip (which is indicative of the surface structure) is not measured by the (heated) tip itself but instead by means of at least one separate heat sensor which is movably mounted with respect to a base plate of the cantilever; this heat sensor, therefore, is no longer influenced by any cooling effects which are due to the area surrounding the tip.

Figure 7:
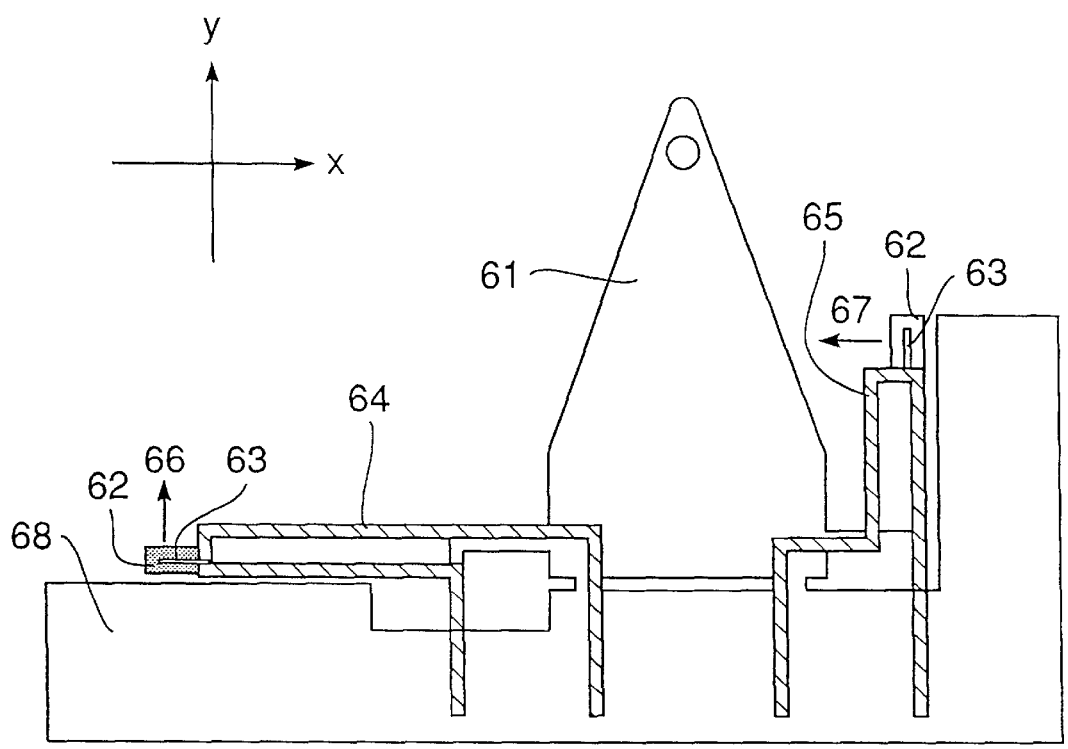
FIG. 7 shows a first embodiment of a sensor which detects the displacement of the cantilever of an AFM.
Figure 8:
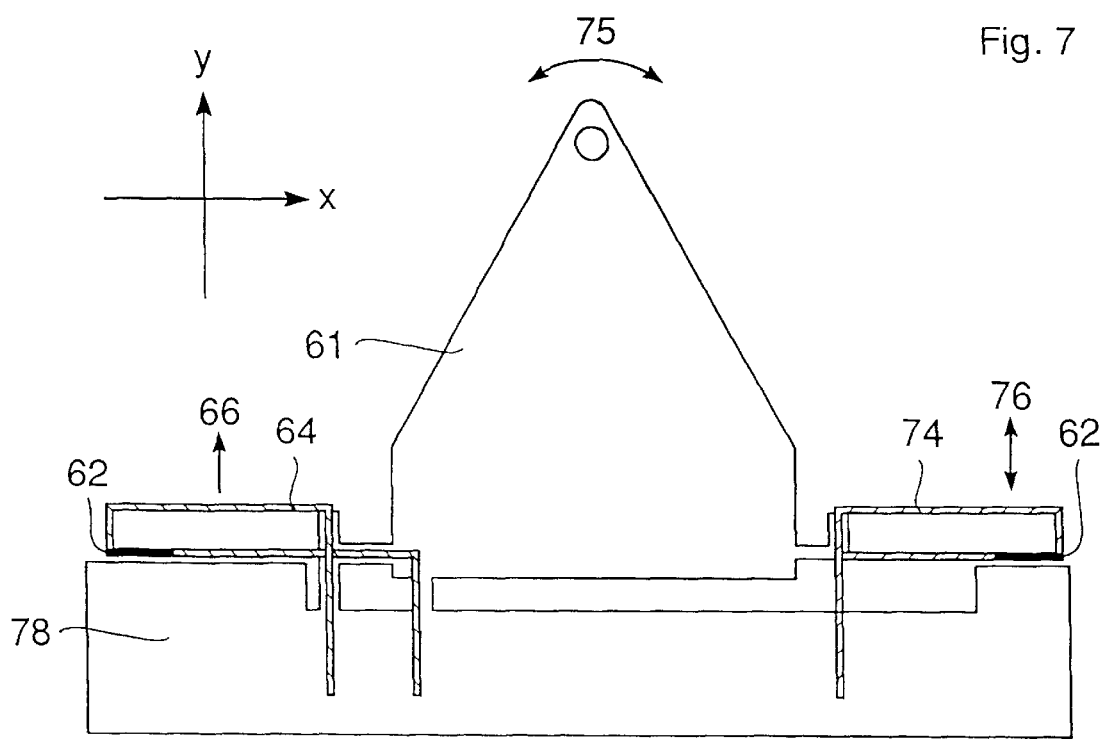
FIG. 8 shows a second embodiment of such a sensor which detects not only the displacement of the cantilever but also any frictional side movement of the cantilever.

According to FIGS. 7 and 8, these two embodiments of a displacement sensor are based on the afore-mentioned basic principle of the present invention, i.e. a heated movable object that creates a temperature gradient which is sensitive to any displacement (deflection or friction) relative to an immovable object, a detecting means being adopted to detect the variation in a resistance value caused by temperature gradient variations.

FIG. 7 shows a first embodiment of a displacement sensor arrangement for an AFM. One end of a cantilever 61 is movable fixed to a base plate 68 of the AFM. The cantilever 61 is fixed in such a way that there are allowed movements of the cantilever perpendicular to the plane of projection whereas any movements in x- or y-direction, as defined by the coordinate axes shown in FIG. 7, are avoided.

The displacement sensor arrangement comprises a coupling means 64, 65 for coupling a heat sensor 62 to the cantilever 61. The heat sensor 62 is a small piece of a semiconductor material with an integrated heater 63. The heater 63 is established by a doped line (which is e.g. made of Si) on the semi-conductor piece and is supplied with a heat current of a predetermined value. The coupling means 64, 65 also provides contact lines to supply the current to the heater 63.

The coupling of the coupling means 64 is configured such that a displacement of the cantilever 61 in the direction perpendicular to the plane of projection is transformed in a displacement of the heat sensor 62 in respect to the base plate 68 that is substantially perpendicular to the displacement of the cantilever 61, i.e. in the y-direction as indicated by arrow 66 in FIG. 7.

The coupling of the coupling means 65 is configured such that a displacement of the cantilever 61 in the direction perpendicular to the plane of projection is transformed in a displacement of the heat sensor 62 in respect to the base plate 68 which is substantially perpendicular to the displacement of the cantilever 61, i.e. in the x-direction as indicated by arrow 67 in FIG. 7.

Any displacement of the cantilever 61 is transformed to a corresponding displacement of the heat sensor 62, the temperature in the close vincinity of the heat sensor 62 therefore varying as the distance between the heat sensor 62 and the base plate 68 varies; this results in a corresponding change of the resistance value which can be easily measured.

Since the two displacement directions (x/y-direction) of the sensor arrangement are substantially perpendicular to each other, the sensor arrangement has the advantage of combining the measured values in order to obtain a more reliable and distinguishable value for the present displacement of the cantilever from the sensor arrangement (superposition principle).

FIG. 8 shows a second embodiment of a displacement sensor arrangement for an AFM according to the invention. With this arrangement, it is possible to additionally measure a displacement of the cantilever 61 which goes back to a friction between the tip and the surface of the sample. To this end, one end portion of a cantilever 61 is movably fixed to a base plate 78 of the AFM. The cantilever 61 is fiexd in such a way that one edge of the cantilever is allowed to be displaced only in that direction which is substantially perpendicular to the plane of projection, whereas the other edge of the cantilever may be displaced substantially in the x-direction as defined by the coordinate axes in FIG. 8.

The displacement sensor arrangement of this second embodiment also comprises a coupling means 64, 74 for coupling a heat sensor 62 to the cantilever 61.

The coupling of the coupling means 74 is configured such that a displacement of the cantilever 61 in x-direction due to friction is transformed to a corresponding displacement of the heat sensor 62 in respect to the base plate 78 which is substantially perpendicular to the displacement of the cantilever 61, i.e. in the y-direction as indicated by arrow 76 in FIG. 8.

With respect to further aspects and advantages of the invention, reference is explicitly made to the disclosure of the drawings.

What is claimed is:

1. Investigation and manipulation device for a sample, said sample consisting of a material which is locally deformed when subjected to a local heat treatment, said device comprising:

an investigation and manipulation tool movably supported by a cantilever, and positioning means for positioning said cantilever and thereby said tool relatively to said sample, characterized by power supply means for supplying electric power to said tool, said tool and said cantilever having such a structure and/or being respectively made of such materials that the supplied power is heating substantially only said tool, and sensing means adapted to supply a low amount of power to said tool, said low amount of power being insufficient to locally deform said sample, said sensing means detecting a variation in temperature of said tool as being indicative of the surface structure of said sample, and manipulation means adapted to supply a high amount of power to said tool, said high amount of power heating said tool to a temperature which is sufficient to deform the sample surface region being presently effected by said tool, said cantilever, in a predetermined small distance to said tool, comprising a cooling region of relatively high heat conductivity so as to provide means for fast cooling said tool.

2. Investigation and manipulation device according to claim 1, characterized in that said power supply means comprises a pair of contact lines provided on a surface portion of said cantilever, the end of each line being electrically connected to said tool.

3. Investigation and manipulation device according to claim 2, characterized in that at least that one region of said cantilever which is in the neighbourhood of said tool is made of a material which has a lower heat conductivity than the material of said tool.

4. Investigation and manipulation device according to claim 3, characterized in that at least said neighboured region of said cantilever is made of $SiO_2$ and said tool is made of doped or not doped Si.

5. Manipulation device for a sample, said sample consisting of a material which is locally deformed when subjected to a local heat treatment, said device comprising:

a manipulation tool movably supported by a cantilever, and positioning means for positioning said cantilever and thereby said tool relatively to said sample, characterized by power supply means for supplying electric power to said tool, said tool and said cantilever having such a structure and/or being respectively made of such materials that the supplied power is heating substantially only said tool, manipulation means adapted to supply a high amount of power to said tool, said high amount of power heating said tool to a temperature which is sufficient to deform the sample surface region being presently affected by said tool, and said cantilever, in a predetermined small distance to said tool, comprising a cooling region of relatively high heat conductivity so as to provide means for fast cooling said tool.

6. Manipulation device according to claim 5, characterized in that said cooling region is a layer provided at that side of said cantilever which is opposing said tool.

7. Manipulation device according to claim 5, characterized in that said cooling region is a layer provided at a side of said cantilever which is not in contact with said pair of contact lines or with said power supply means.

8. Investigation and manipulation device according to claim 2, characterized in that said cantilever is made of two arms, said two arms being spaced from each other and made of electrically conductive material, each arm, at the outer end thereof, being connected to said tool so as to supply electric power to said tool, said two arms thus being an integrated part of said power supply means.

9. Investigation and manipulation device according to claim 8, characterized in that said two arms of said cantilever are relatively narrow at those parts which are contacting the tip and relatively broad at the other parts thereof.

10. Investigation and manipulation device according to claim 8, characterized in that said tool is made of doped or not doped Si.

11. Investigation and manipulation device according to claim 1, characterized in that said sensing means is detecting a variation in the temperature of said tool by measuring the corresponding variation of the power supplied to said tool.

12. Investigation and manipulation device according to claim 1, characterized in that said tool is a tip similar to a tip used in an atomic force microscope (AFM).

13. Investigation and manipulation device according to claim 1, characterized in that said sample is a storage medium in the form of a thin soft layer, the manipulation means forming storage pits of predetermined size at predetermined storage locations and the sensing means sensing as to whether each predetermined storage location comprises a pit or not.

14. Investigation and manipulation device according to claim 13, characterized in that said thin soft layer is a layer made of PMMA in a thickness of about 30 nm.

15. Data storage system, comprising:

a plurality of support means being arranged in the form of a matrix, each support means having a read/write tip mounted thereon, and positioning means for positioning said matrix relative to the surface of a storage medium having a storage surface consisting of a material which is locally deformed when subjected to a local heat treatment, each deformation defining one storage pit, characterized by power supply means for supplying electric power to each read/write tip of said matrix, each tip and support means being formed in such a way that the supplied power is heating substantially only the tip and a region of relatively high heat conductivity provides fast cooling of the tip when power is not supplied to said each tip, reading means adapted to supply a low amount of power to said tip, said low amount of power being insufficient to form a pit on said storage medium, said reading means being further adapted to individually detect a variation in temperature of each of said tips as being indicative of the presence or absence of a pit, and writing means adapted to individually supply a high amount of power to each of said tips, said high amount of power heating the respective tip to a temperature which is sufficient to form a storage pit at that surface region of said storage medium which is presently affected by said tip.

16. Data storage system according to claim 15, characterized in that said support means is a cantilever.

17. Data storage system according to claim 16, characterized in that said reading means detects a variation in the temperature of each of said tips by measuring the corresponding variation of the power supplied to the respective tip.

18. Data storage system according to claim 16, characterized in that said storage surface of said storage medium is a thin layer made of PMMA in a thickness of preferably 30 nm.

19. Data storage system according to claim 16, characterized in that it is designed for said storage medium having the form of a disk.

20. Data storage system, comprising:
    a plurality of cantilevers being arranged in the form of a matrix, each cantilever having a read/write tip mounted thereon, and
    positioning means for positioning said matrix relative to the surface of a storage medium having a storage surface consisting of a material which is locally deformed when subjected to a local heat treatment, each deformation defining one storage pit, said storage medium having the form of a disk,
characterized by
    power supply means for supplying electric power to each read/write tip of said matrix, each tip and cantilever being formed in such a way that the supplied power is heating substantially only the tip,
    reading means adapted to supply a low amount of power to said tip, said low amount of power being insufficient to form a pit on said storage medium, said reading means being further adapted to individually detect a variation in temperature of each of said tips as being indicative of the presence or absence of a pit, and
    writing means adapted to individually supply a high amount of power to each of said tips, said high amount of power heating the respective tip to a temperature which is sufficient to form a storage pit at that surface region of said storage medium which is presently affected by said tip,
    wherein said positioning means is formed by a swivel arm for moving said matrix relative to the surface of the disk and by a motor for turning said disk.

21. Data storage system according to claim 20, characterized in that it is designed for a plurality of storage media arranged on top of each other forming a stack of storage disks.

22. Sensor for detecting displacement of an AFM cantilever. comprising:
    a sensor cantilever coupled to the AFM cantilever in such a way that the displacement of the AFM cantilever is transferred to a corresponding displacement of the sensor cantilever;
    heating means for heating the sensor cantilever to a predetermined temperature so as to provide a specific temperature gradient around the sensor cantilever; and
    detecting means for detecting variations in the temperature gradient caused by a displacement of the sensor cantilever.

23. Sensor according to claim 22, characterized in that the sensor cantilever is movably coupled in such a way that the sensor is displaced relatively to a base plate of the AFM cantilever, this displacment being proportional to the displacement of the AFM cantilever relative to an investigated object.

24. Sensor according to claim 23, characterized in that the sensor cantilever is movably coupled in such a way that the sensor is displaced in a direction which is substantially perpendicular to the displacement direction of the AFM cantilever.

25. Sensor according to claim 23, characterized in that there are provided two sensor cantilevers, these two sensors being coupled to the AFM cantilever in such a way that their displacement is substantially perpendicular to the displacement direction of the AFM cantilever and substantially perpendicular to that of the other sensor.

* * * * *